(12) United States Patent
Halbfinger

(10) Patent No.: US 11,993,631 B2
(45) Date of Patent: May 28, 2024

(54) PROCESS FOR MANUFACTURING PEPTIDE

(71) Applicant: BioLineRx Ltd., Modiln (IL)

(72) Inventor: Efrat Halbfinger, RaAnana (IL)

(73) Assignee: BioLineRx Ltd., Modiln (IL)

( * ) Notice: Subject to any disclaimer, the term of this patent is extended or adjusted under 35 U.S.C. 154(b) by 0 days.

(21) Appl. No.: 18/270,509

(22) PCT Filed: Dec. 29, 2021

(86) PCT No.: PCT/IL2021/051549
§ 371 (c)(1),
(2) Date: Jun. 30, 2023

(87) PCT Pub. No.: WO2022/144886
PCT Pub. Date: Jul. 7, 2022

(65) Prior Publication Data
US 2024/0092827 A1    Mar. 21, 2024

Related U.S. Application Data

(60) Provisional application No. 63/131,873, filed on Dec. 30, 2020.

(51) Int. Cl.
| | | |
|---|---|---|
| C07K 7/00 | (2006.01) | |
| C07K 1/04 | (2006.01) | |
| C07K 1/10 | (2006.01) | |
| C07K 1/20 | (2006.01) | |

(52) U.S. Cl.
CPC ............. *C07K 1/20* (2013.01); *C07K 1/042* (2013.01); *C07K 1/10* (2013.01)

(58) Field of Classification Search
CPC ......... C07K 14/375; A61P 31/20; A61P 35/00
See application file for complete search history.

(56) References Cited

U.S. PATENT DOCUMENTS

| | | | |
|---|---|---|---|
| 7,138,488 B2 | 11/2006 | Fujii | |
| 7,423,007 B2 | 9/2008 | Fujii et al. | |
| 8,017,585 B2 | 9/2011 | Fujii et al. | |
| 8,435,939 B2 | 5/2013 | Fujii et al. | |
| 2013/0303460 A1 | 11/2013 | Pelled | |

FOREIGN PATENT DOCUMENTS

| | | |
|---|---|---|
| WO | WO 2008/075369 | 6/2008 |
| WO | WO 2008/075370 | 6/2008 |
| WO | WO 2010/146578 | 12/2010 |
| WO | WO 2012/095849 | 7/2012 |
| WO | WO 2013/160895 | 10/2013 |
| WO | WO 2022/144885 | 7/2022 |
| WO | WO 2022/144886 | 7/2022 |

OTHER PUBLICATIONS

International Search Report and the Written Opinion dated Mar. 14, 2022 From the International Searching Authority Re. Application No. PCT/IL2021/051548. (18 Pages).
International Search Report and the Written Opinion dated Mar. 15, 2022 From the International Searching Authority Re. Application No. PCT/IL2021/051549. (13 Pages).
Abraham et al. "Enhanced Unique Pattern of Hematopoietic Cell Mobilization Induced by the CXCR4 Antagonist 4F-Benzoyl-TN14003", Stem Cells, 25(9): 2158-2166, Published Online May 24, 2007.
Martin et al. "Greening the Synthesis of Peptide Therapeutics: an Industrial Perspective", RSC Advances, 10: 42457-42492, Nov. 24, 2020.
International Preliminary Report on Patentability dated Jul. 13, 2023 From the International Bureau of WIPO Re. Application No. PCT/IL2021/051548 (12 Pages).
International Preliminary Report on Patentability dated Jul. 13, 2023 From the International Bureau of WIPO Re. Application No. PCT/IL2021/051549 (7 Pages).
Official Action Dated Feb. 16, 2024 from the US Patent and Trademark Office Re. U.S. Appl. No. 18/537,973. (12 pages).

*Primary Examiner* — Jeanette M Lieb

(57) ABSTRACT

A large-scale process is described herein for preparing a cyclic peptide as described, comprising solid phase peptide synthesis of a linear peptide and cleaving it from the resin; oxidizing cysteine residues to form an intramolecular disulfide bond; and isolating the cyclic peptide, wherein:
(i) coupling uses diisopropylcarbodiimide and ethyl cyanohydroxyiminoacetate and/or N-hydroxybenzotriazole;
(ii) cleaving comprises contacting the peptide with a solution comprising TFA and dithioerythritol and/or dithiothreitol;
(iii) the peptide is precipitated after cleaving without prior concentration of the peptide by evaporation;
(iv) oxidizing comprises contacting an aqueous solution comprising at least 5 mg/mL peptide with hydrogen peroxide;
(v) isolating comprises loading the peptide on a reverse phase chromatography at up to 40 grams/kg column, and elution from the column;
(vi) isolating comprises lyophilization, followed by grinding the peptide; and/or
(vii) substitution of the resin is at least 0.3 milliequivalents/gram, and/or the resin is a Rink aminomethylstyrene resin.

15 Claims, 1 Drawing Sheet
Specification includes a Sequence Listing.

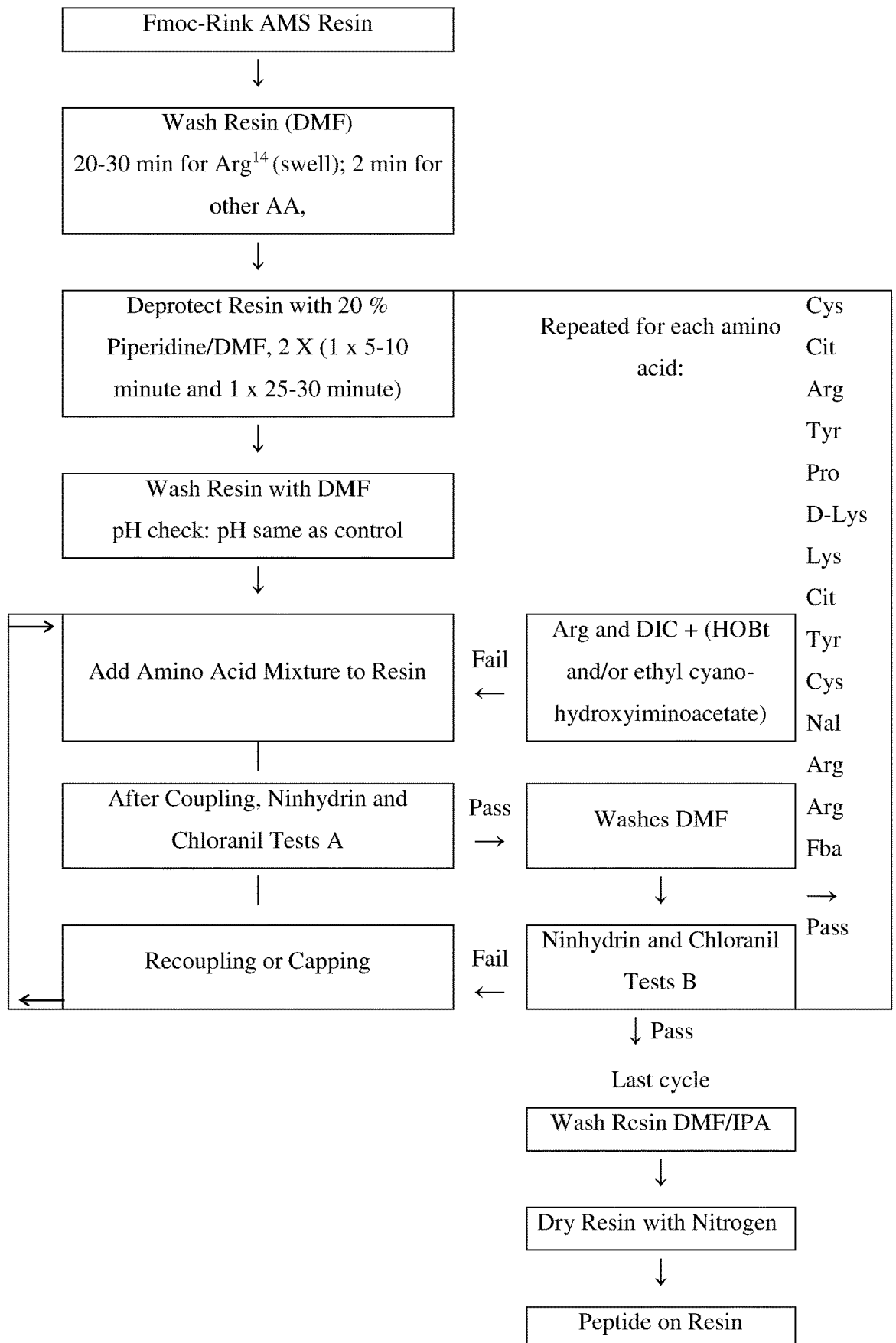

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: X=naphthylalanine
<220> FEATURE:
<221> NAME/KEY: MOD_RES
<222> LOCATION: (6)..(6)
<223> OTHER INFORMATION: X=citrulline
<220> FEATURE:
<221> NAME/KEY: MOD_RES
<222> LOCATION: (8)..(8)
<223> OTHER INFORMATION: X=D-lysine
<220> FEATURE:
<221> NAME/KEY: MOD_RES
<222> LOCATION: (12)..(12)
<223> OTHER INFORMATION: X=citrulline
<220> FEATURE:
<221> NAME/KEY: MOD_RES
<222> LOCATION: (14)..(14)
<223> OTHER INFORMATION: amidated

<400> SEQUENCE: 1

Arg Arg Xaa Cys Tyr Xaa Lys Xaa Pro Tyr Arg Xaa Cys Arg
1               5                   10
```

PROCESS FOR MANUFACTURING PEPTIDE

RELATED APPLICATIONS

This application is a National Phase of PCT Patent Application No. PCT/IL2021/051549 having International filing date of Dec. 29, 2021, which claims the benefit of priority under 35 USC § 119(e) of U.S. Provisional Patent Application No. 63/131,873 filed on Dec. 30, 2020. The contents of the above applications are all incorporated by reference as if fully set forth herein in their entirety.

SEQUENCE LISTING STATEMENT

The ASCII file, entitled 95788 SequenceListing.txt, created on Jun. 30, 2023, comprising 873 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to chemical synthesis, and more particularly, but not exclusively, to a novel process of preparing peptides such as BL-8040, which are usable, for example, in treating conditions such as cancer and/or arthritis.

BL-8040 is a peptide also known as 4F-benzoyl-TN14003 (4-fluoro-benzoyl-Arg-Arg-Nal-Cys-Tyr-Cit-Lys-DLys-Pro-Tyr-Arg-Cit-Cys-Arg-NH$_2$, SEQ ID NO: 1), and is cyclic upon formation of a disulfide bond between the two Cys residues thereof.

U.S. Pat. No. 7,423,007 describes peptides having CXC4 antagonism; including 4F-benzoyl-TN14003. According to the teachings of U.S. Pat. No. 7,423,007, 4F-benzoyl-TN14003 is manufactured by solid phase synthesis using DIPCDI-HOBt as a coupling agent, in DMF (with amino acids added at 2.5 equivalents), followed by deprotection and cleavage using 1 M TMSBr-thioanisole/TFA with m-cresol and ethanedithiol, and cyclization by air oxidation.

Additional background art includes U.S. Pat. Nos. 7,138,488 and 8,435,939, and International Patent Application Publications WO 2008/075369, WO 2008/075370, WO 2010/146578, WO 2012/095849 and WO 2013/160895.

SUMMARY OF THE INVENTION

According to an aspect of some embodiments of the invention, there is provided a large-scale process of preparing a cyclic peptide having SEQ ID NO: 1, or a pharmaceutically acceptable salt thereof, the process comprising:
(a) sequentially coupling amino acids and 4-fluorobenzoic acid to a resin by solid phase peptide synthesis, thereby obtaining a linear peptide coupled to the resin;
(b) cleaving the linear peptide from the resin, thereby obtaining a free linear peptide;
(c) oxidizing cysteine residues of the linear peptide to form an intramolecular disulfide bond, thereby obtaining the cyclic peptide having SEQ ID NO: 1 in solution; and
(d) isolating the cyclic peptide having SEQ ID NO: 1, or a pharmaceutically acceptable salt thereof, wherein:
(i) the coupling is effected using diisopropylcarbodiimide (DIC) in combination with ethyl cyanohydroxyiminoacetate and/or N-hydroxybenzotriazole;
(ii) the cleaving is effected by contacting the linear peptide coupled to the resin with a solution comprising trifluoroacetic acid (TFA) and a scavenger selected from the group consisting of dithioerythritol (DTE) and dithiothreitol (DTT);
(iii) the process further comprises precipitating the free linear peptide after cleaving without concentrating the free linear peptide by evaporation prior to precipitating;
(iv) the oxidizing is effected by contacting an aqueous solution comprising the linear peptide at a concentration of at least 5 mg/mL with hydrogen peroxide;
(v) the isolating comprises loading the cyclic peptide on a reverse phase chromatography column at a concentration of no more than 40 grams cyclic peptide per kg of the column, and eluting the cyclic peptide from the column;
(vi) isolating the cyclic peptide having SEQ ID NO: 1 comprises lyophilization, and the process further comprises grinding the cyclic peptide following lyophilization; and/or
(vii) a degree of substitution of the resin is at least 0.3 milliequivalents per gram, and/or the resin is a Rink aminomethylstyrene (AMS) resin.

According to an aspect of some embodiments of the invention, there is provided a large-scale process of preparing a cyclic peptide having SEQ ID NO: 1, or a pharmaceutically acceptable salt thereof, the process comprising:
(a) sequentially coupling amino acids and 4-fluorobenzoic acid to a resin by solid phase peptide synthesis, using diisopropylcarbodiimide (DIC) in combination with ethyl cyanohydroxyiminoacetate and/or N-hydroxybenzotriazole, thereby obtaining a linear peptide coupled to the resin;
(b) cleaving the linear peptide from the resin, thereby obtaining a free linear peptide;
(c) oxidizing cysteine residues of the linear peptide to form an intramolecular disulfide bond, thereby obtaining the cyclic peptide having SEQ ID NO: 1 in solution; and
(d) isolating the cyclic peptide having SEQ ID NO: 1, or a pharmaceutically acceptable salt thereof.

According to an aspect of some embodiments of the invention, there is provided a large-scale process of preparing a cyclic peptide having SEQ ID NO: 1, or a pharmaceutically acceptable salt thereof, the process comprising:
(a) sequentially coupling amino acids and 4-fluorobenzoic acid to a resin by solid phase peptide synthesis, thereby obtaining a linear peptide coupled to the resin;
(b) cleaving the linear peptide from the resin by contacting the linear peptide coupled to the resin with a solution comprising trifluoroacetic acid (TFA) and a scavenger selected from the group consisting of dithioerythritol (DTE) and dithiothreitol (DTT), thereby obtaining a free linear peptide;
(c) oxidizing cysteine residues of the linear peptide to form an intramolecular disulfide bond, thereby obtaining the cyclic peptide having SEQ ID NO: 1 in solution; and
(d) isolating the cyclic peptide having SEQ ID NO: 1, or a pharmaceutically acceptable salt thereof.

According to an aspect of some embodiments of the invention, there is provided a large-scale process of preparing a cyclic peptide having SEQ ID NO: 1, or a pharmaceutically acceptable salt thereof, the process comprising:
  (a) sequentially coupling amino acids and 4-fluorobenzoic acid to a resin by solid phase peptide synthesis, thereby obtaining a linear peptide coupled to the resin;
  (b) cleaving the linear peptide from the resin, thereby obtaining a free linear peptide, and precipitating the free linear peptide after cleaving without concentrating the free linear peptide by evaporation prior to precipitating;
  (c) oxidizing cysteine residues of the linear peptide to form an intramolecular disulfide bond, thereby obtaining the cyclic peptide having SEQ ID NO: 1 in solution; and
  (d) isolating the cyclic peptide having SEQ ID NO: 1, or a pharmaceutically acceptable salt thereof.

According to an aspect of some embodiments of the invention, there is provided a large-scale process of preparing a cyclic peptide having SEQ ID NO: 1, or a pharmaceutically acceptable salt thereof, the process comprising:
  (a) sequentially coupling amino acids and 4-fluorobenzoic acid to a resin by solid phase peptide synthesis, thereby obtaining a linear peptide coupled to the resin;
  (b) cleaving the linear peptide from the resin, thereby obtaining a free linear peptide;
  (c) oxidizing cysteine residues of the linear peptide to form an intramolecular disulfide bond, the oxidizing being effected by contacting an aqueous solution comprising the linear peptide at a concentration of at least 5 mg/mL with hydrogen peroxide, thereby obtaining the cyclic peptide having SEQ ID NO: 1 in solution; and
  (d) isolating the cyclic peptide having SEQ ID NO: 1, or a pharmaceutically acceptable salt thereof.

According to an aspect of some embodiments of the invention, there is provided a large-scale process of preparing a cyclic peptide having SEQ ID NO: 1, or a pharmaceutically acceptable salt thereof, the process comprising:
  (a) sequentially coupling amino acids and 4-fluorobenzoic acid to a resin by solid phase peptide synthesis, thereby obtaining a linear peptide coupled to the resin;
  (b) cleaving the linear peptide from the resin, thereby obtaining a free linear peptide;
  (c) oxidizing cysteine residues of the linear peptide to form an intramolecular disulfide bond, thereby obtaining the cyclic peptide having SEQ ID NO: 1 in solution; and
  (d) isolating the cyclic peptide having SEQ ID NO: 1, or a pharmaceutically acceptable salt thereof, wherein isolating comprises loading the cyclic peptide on a reverse phase chromatography column at a concentration of no more than 40 grams cyclic peptide per kg of the column, and eluting the cyclic peptide from the column.

According to an aspect of some embodiments of the invention, there is provided a large-scale process of preparing a cyclic peptide having SEQ ID NO: 1, or a pharmaceutically acceptable salt thereof, the process comprising:
  (a) sequentially coupling amino acids and 4-fluorobenzoic acid to a resin by solid phase peptide synthesis, wherein a degree of substitution of the resin is at least 0.3 milliequivalents per gram and/or the resin is a Rink aminomethylstyrene (AMS) resin, thereby obtaining a linear peptide coupled to the resin;
  (b) cleaving the linear peptide from the resin, thereby obtaining a free linear peptide;
  (c) oxidizing cysteine residues of the linear peptide to form an intramolecular disulfide bond, thereby obtaining the cyclic peptide having SEQ ID NO: 1 in solution; and
  (d) isolating the cyclic peptide having SEQ ID NO: 1, or a pharmaceutically acceptable salt thereof.

According to some of any of the respective embodiments described herein, the coupling is effected using diisopropylcarbodiimide (DIC) in combination with ethyl cyanohydroxyiminoacetate and/or N-hydroxybenzotriazole.

According to some of any of the embodiments described herein relating to coupling with DIC and ethyl cyanohydroxyiminoacetate and/or N-hydroxybenzotriazole, the DIC and the ethyl cyanohydroxyiminoacetate and/or N-hydroxybenzotriazole are used in a molar excess of about two-fold.

According to some of any of the respective embodiments described herein, the cleaving is effected by contacting the linear peptide coupled to the resin with a solution comprising trifluoroacetic acid (TFA) and a scavenger selected from the group consisting of dithioerythritol (DTE) and dithiothreitol (DTT).

According to some of any of the embodiments described herein relating to cleaving with a solution comprising a scavenger selected from the group consisting of dithioerythritol and dithiothreitol, a concentration of the scavenger in the solution is in a range of from 10 mg/mL to 500 mg/mL.

According to some of any of the embodiments described herein relating to cleaving with a solution comprising dithiothreitol, a concentration of dithiothreitol in the solution is about 50 mg/mL.

According to some of any of the respective embodiments described herein, the process further comprises precipitating the free linear peptide after the cleaving without concentrating the free linear peptide by evaporation prior to precipitating.

According to some of any of the embodiments described herein relating to precipitating a linear peptide, precipitating is effected by addition of a mixture of tert-butyl methyl ether (MTBE) and hexane at a volume of about 45 mL of the mixture per gram of the resin.

According to some of any of the respective embodiments described herein, the oxidizing is effected by contacting the linear peptide with hydrogen peroxide.

According to some of any of the embodiments described herein relating to contacting a linear peptide with hydrogen peroxide, contacting is effected by contacting an aqueous solution comprising the linear peptide at a concentration of at least 5 mg/mL with hydrogen peroxide.

According to some of any of the respective embodiments described herein, isolating comprises loading the cyclic peptide on a reverse phase chromatography column at a concentration of no more than 40 grams cyclic peptide per kg of the column, and eluting the cyclic peptide from the column.

According to some of any of the embodiments described herein relating to a reverse phase chromatography column, the column is a C18 column.

According to some of any of the embodiments described herein relating to eluting, the eluting is effected with triethylammonium phosphate solution.

According to some of any of the respective embodiments described herein, isolating the cyclic peptide having SEQ ID NO: 1 comprises lyophilization, and the process further comprises grinding the cyclic peptide following lyophilization.

According to some of any of the respective embodiments described herein, a degree of substitution of the resin solid phase peptide synthesis is at least 0.3 milliequivalents per gram and/or the resin is a Rink aminomethylstyrene (AMS) resin.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING

Some embodiments of the invention are herein described, by way of example only, with reference to the accompanying drawing. With specific reference now to the drawing in detail, it is stressed that the particulars shown are by way of example and for purposes of illustrative discussion of embodiments of the invention. In this regard, the description taken with the drawing makes apparent to those skilled in the art how embodiments of the invention may be practiced.

In the drawing:

FIG. 1 presents a flow diagram for the solid phase synthesis portion of a process of preparing BL-8040 according to some exemplary embodiments of the invention, comprising sequential cycles for coupling of Cys, Cit (citrulline), Arg, Tyr, Pro, D-Lys, Lys, Cit, Tyr, Cys, Nal (naphthylalanine), Arg, Arg and Fba (4-fluoro-benzoic acid) to a resin.

DESCRIPTION OF SPECIFIC EMBODIMENTS OF THE INVENTION

The present invention, in some embodiments thereof, relates to chemical synthesis, and more particularly, but not exclusively, to a novel process of preparing peptides such as BL-8040, which are usable, for example, in treating conditions such as cancer and/or arthritis.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Peptides are commonly prepared by solid phase synthesis, in which the peptide (in a protected form) is formed attached to a resin and then cleaved from the resin (while removing protecting groups). Intramolecular disulfide bonds, such as in BL-8040 (4-fluoro-benzoyl-Arg-Arg-Nal-Cys-Tyr-Cit-Lys-DLys-Pro-Tyr-Arg-Cit-Cys-Arg-NH$_2$, SEQ ID NO: 1), are then formed by oxidation of Cys residues.

Following laborious experimentation, the inventor has uncovered novel processes which are surprisingly effective for large-scale syntheses of such peptides, and BL-8040 in particular.

According to an aspect of some embodiments of the invention, there is provided a process of preparing a cyclic peptide comprising an intramolecular disulfide bond, or a pharmaceutically acceptable salt thereof. In some of any of the embodiments described herein, the cyclic peptide has SEQ ID NO: 1 (4-fluoro-benzoyl-Arg-Arg-Nal-Cys-Tyr-Cit-Lys-DLys-Pro-Tyr-Arg-Cit-Cys-Arg-NH$_2$), and the Cys residues are linked by an intramolecular disulfide bond. The peptide may also be an analog or derivative of the peptide having SEQ ID NO: 1.

The process comprises sequentially coupling amino acids, and optionally an amino acid analog (e.g., an N-terminal carboxylic acid, such as 4-fluoro-benzoic acid) if present in the peptide, to a resin (e.g., Rink AMS resin) by solid phase peptide synthesis (according to general procedures known in the art), to obtain a linear peptide coupled to the resin.

The process further comprises cleaving the peptide formed by coupling from the resin, thereby obtaining a free (linear) peptide (according to any of the respective embodiments described herein), and oxidizing cysteine residues of the linear peptide to form an intramolecular disulfide bond (according to any of the respective embodiments described herein), thereby obtaining the cyclic peptide (in solution).

In some of any of the embodiments described herein, the process is a large-scale process.

Herein, the term "large-scale process" refers to a process for preparation of at least 100 grams of a final product (in a single run of the process).

In some of any of the embodiments described herein relating to a large-scale process, at least 250 grams of cyclic peptide are prepared, or at least 500 grams of peptide, or at least 1 kg of peptide, or at least 3 kg of peptide, or even at least 10 kg of cyclic peptide are prepared by the process.

Coupling:

The order of the sequential coupling begins from the C-terminus and ends with the N-terminus. For example, for SEQ ID NO: 1, the order of sequential coupling is Arg, Cys, Cit (citrulline), Arg, Tyr, Pro, DLys (D-lysine), Lys, Cit, Tyr, Cys, Nal (naphthylalanine), Arg, Arg, 4-fluoro-benzoic acid.

Coupling comprises forming an amide bond between a carboxylate group (e.g., of an amino acid or N-terminal carboxylic acid) and an amine group (e.g., of a resin in the first step or an N-terminus in subsequent steps), and is preferably effected using one or more coupling reagents known in the art to be suitable for amide bond formation, for example, a carbodiimide (e.g., 1-ethyl-3-(3-dimethylaminopropyl)carbodiimide, dicyclohexylcarbodiimide and/or diisopropylcarbodiimide), aminium/uronium (e.g., HATU, HBTU, TBTU and/or HCTU) or phosphonium salt (e.g., PyBOP and/or PyAOP) and/or propanephosphonic acid anhydride.

In some of any of the embodiments described herein, the one or more coupling reagents comprises a carbodiimide (e.g., diisopropylcarbodiimide) and an additional agent (e.g., in about the same molar concentration as the carbodiimide) such as a hydroxytriazole (e.g., N-hydroxybenzotriazole (HOBt) or 1-hydroxy-7-azabenzotriazole (HOAt) and/or a cyanohydroxyiminoacetate ester (e.g., ethyl cyanohydroxyiminoacetate).

In some of any of the embodiments described herein, coupling is effected using a carbodiimide and a cyanohydroxyiminoacetate ester. In some such embodiments, the carbodiimide and/or the cyanohydroxyiminoacetate ester are used in a molar excess of about two-fold (relative to the amino acid or other carboxylic acid being coupled).

In some of any of the embodiments described herein, coupling is effected using a carbodiimide with ethyl cyanohydroxyiminoacetate and/or N-hydroxybenzotriazole. In some such embodiments, the carbodiimide and/or the ethyl cyanohydroxyiminoacetate and/or N-hydroxybenzotriazole are used in a molar excess of about two-fold (relative to the amino acid or other carboxylic acid being coupled).

In some of any of the embodiments described herein, coupling is effected using diisopropylcarbodiimide (DIC) with ethyl cyanohydroxyiminoacetate and/or N-hydroxybenzotriazole. In some such embodiments, the DIC and the ethyl cyanohydroxyiminoacetate and/or N-hydroxybenzotriazole are used in a molar excess of about two-fold (relative to the amino acid or other carboxylic acid being coupled).

Without being bound by any particular theory, it is believed that the use of ethyl cyanohydroxyiminoacetate in combination with a carbodiimide (e.g., in proportions described herein) is particularly suitable for a large scale synthesis of a peptide described herein, e.g., as compared with hydroxytriazoles.

At each amino acid coupling step, the N-terminus of the amino acid is protected by a readily removable group, preferably fluorenylmethyloxycarbonyl (Fmoc), which may optionally be cleaved by a mild base such as piperidine (e.g., 20-50% piperidine in DMF). An exemplary concentration of piperidine in DMF is about 20%.

For example, Fmoc groups may optionally be removed by washing twice in piperidine solution (according to any of the embodiments described herein), optionally once for 5-10 minutes and then optionally once for 25-30 minutes; followed by washing of the resin (e.g., in DMF without piperidine) to remove the base (which may optionally be ascertained by determining pH).

In addition, side chains of certain amino acids may be protected by a readily removable group (which is not cleaved by the abovementioned mild base), such as t-butoxy. Thus, side chain hydroxy groups (e.g., in Tyr, Ser and Thr) and/or carboxylate groups (e.g., in Asp and Glu) may preferably be protected by t-butyl (t-Bu) (to form a t-butoxy group), and side chain amine groups (e.g., in Lys, Trp and His) may be protected by t-butoxycarbonyl (Boc) (which comprises a t-butoxy group); and in both cases, cleavage (e.g., in an acidic environment) may regenerate the unprotected hydroxy or amine group. Similarly, side chain thiohydroxy groups (e.g., of Cys) and/or carboxylate groups (e.g., in Asp and Glu) and may preferably be protected with trityl (Trt), and/or side chain guanidinium groups (e.g., of Arg) may preferably be protected with 2,2,4,6,7-pentamethyl-2,3-dihydrobenzofuran-5-sulfonyl (Pbf); each of which may optionally be cleaved in an acidic environment.

The aforementioned side chain protective groups are known for being particularly compatible with the use of Fmoc. The skilled person will be aware of additional protective groups suitable for specific groups in amino acid side chains, and their compatibility with each other and with various N-terminal protective groups.

In some of any of the embodiments described herein, the resin to which the amino acids are sequentially coupled is a Rink aminomethylstyrene (AMS) resin (aminomethylstyrene resin substituted with a Rink linker). The Rink AMS resin is optionally protected by Fmoc groups, which may be removed prior to coupling so as to expose amine groups (to which the first amino acid is coupled).

In some of any of the embodiments described herein, the degree of substitution of the resin (to which the amino acids are sequentially coupled) is at least 0.3 milliequivalents per gram resin (e.g., from 0.3 to 1.1 milliequivalents per gram resin), optionally from 0.6 to 1.1 milliequivalents per gram resin, and optionally from 0.6 to 0.9 milliequivalents per gram resin. In some such embodiments, the resin is a Rink AMS resin.

The resin is optionally washed (e.g., once or twice) with a solvent such as dimethylformamide (DMF) prior to each coupling step, for example, to facilitate swelling of the resin. In some exemplary embodiments, the resin is washed for 20-30 minutes prior to deprotection of the resin (e.g., removal of Fmoc groups according to any of the respective embodiments described herein) and coupling of the first amino acid, and washed (e.g., twice) for about 2 minutes prior to each subsequent coupling step.

Cleavage from Resin:

Upon formation of a peptide attached to a resin by sequential coupling according to any of the respective embodiments described herein, the obtained peptide is cleaved from the resin (e.g., according to any of the respective embodiments described herein).

Cleavage of the peptide from the resin (and any protecting groups from the amino acid side chains) is preferably effected by contacting the peptide (coupled to the resin) with a liquid comprising an acid such as trifluoroacetic acid (TFA). The concentration of TFA in the liquid is optionally at least about 80%, or at least about 90%, or at least about 95% by weight, e.g., wherein the balance is primarily water. In exemplary embodiments, the concentration of TFA in the liquid is about 95% by weight, and the balance is primarily water.

The liquid (e.g., acidic liquid according to any of the respective embodiments described herein) used for cleavage optionally further comprises a scavenger (e.g., a scavenger of reactive cationic species which may form during cleavage), such as thiols (e.g., ethanedithiol, dithioerythritol, dithiothreitol), trialkylsilanes, (e.g., triisopropylsilane), phenols (e.g., m-cresol) and/or water.

In some of any of the embodiments described herein, the scavenger in the liquid (e.g., acidic liquid according to any of the respective embodiments described herein) used for cleavage is dithiothreitol (DTT) and/or dithioerythritol (DTE). In some such embodiments, the liquid is a solution comprising TFA (e.g., at a concentration described herein) and DTT and/or DTE, preferably in combination with water.

In some of any of the embodiments described herein relating to DTT and/or DTE, a (total) concentration of DTT and/or DTE in a solution used for cleavage is at least 10 mg/mL. In some such embodiments, the concentration of DTT and/or DTE is in a range of from 10 to 500 mg/mL. In some such embodiments, the concentration of DTT and/or DTE is in a range of from 10 to 200 mg/mL. In some such embodiments, the concentration of DTT and/or DTE is in a range of from 10 to 100 mg/mL. In some such embodiments, the concentration of DTT and/or DTE is in a range of from 10 to 50 mg/mL. An exemplary concentration of DTT is about 50 mg/mL.

In some of any of the embodiments described herein relating to DTT and/or DTE, a (total) concentration of DTT and/or DTE in a solution used for cleavage is at least 25 mg/mL. In some such embodiments, the concentration of DTT and/or DTE is in a range of from 25 to 500 mg/mL. In some such embodiments, the concentration of DTT and/or DTE is in a range of from 25 to 200 mg/mL. In some such embodiments, the concentration of DTT and/or DTE is in a range of from 25 to 100 mg/mL. In some such embodiments, the concentration of DTT and/or DTE is in a range of from 25 to 50 mg/mL.

In some of any of the embodiments described herein relating to DTT and/or DTE, a (total) concentration of DTT and/or DTE in a solution used for cleavage is at least 50 mg/mL. In some such embodiments, the concentration of DTT and/or DTE is in a range of from 50 to 500 mg/mL. In some such embodiments, the concentration of DTT and/or DTE is in a range of from 50 to 200 mg/mL. In some such embodiments, the concentration of DTT and/or DTE is in a range of from 50 to 100 mg/mL.

Upon cleavage of the peptide form the resin, the free peptide is preferably precipitated, for example, by addition of a liquid in which the peptide is insoluble. Precipitation is optionally preceded by concentrating the free peptide by evaporation of a portion of solvent of the solution, thus reducing a volume of the solution (e.g., by about 65% to about 70%). Alternatively, no concentration of free peptide is performed prior to precipitation.

In some of any of the embodiments described herein, precipitation of the free peptide is performed without concentrating the free peptide prior to precipitation.

Precipitation of the peptide, according to any of the respective embodiments described herein, is optionally effected by addition of a dialkyl ether, such as tert-butyl methyl ether (MTBE).

The MTBE is optionally admixed with hexane. In some embodiments, the mixture of MTBE and hexane (optionally chilled, e.g., to a temperature in a range of about 5° C. to about 15° C.) is added to the peptide at a volume of at least 40 mL mixture per gram of resin, and optionally about 45 mL mixture per gram of resin. Exemplary mixtures of MTBE and hexane are composed of MTBE and hexane at a 60:40 (MTBE:hexane) volume ratio.

The precipitated peptide is optionally dried, for example, by lyophilization or by vacuum. In exemplary embodiments, drying is effected by vacuum.

Disulfide Bond Formation:

As discussed herein, an intramolecular disulfide bond is formed (resulting in cyclization of the peptide) by oxidizing cysteine residues of the peptide (which may optionally be formed using any of the embodiments described herein relating to coupling and any of the embodiments describes herein relating to cleavage of the peptide from a resin). Any suitable technique known in the art may optionally be used.

In some of any of the respective embodiments described herein, the oxidizing is effected by contacting the peptide with hydrogen peroxide, for example, by gradual (e.g., dropwise) addition of a hydrogen peroxide solution (e.g., about 1.5% by weight hydrogen peroxide in water). The molar ratio of hydrogen peroxide to pair of Cys residues (e.g., to peptide, wherein the peptide comprises exactly two Cys residues, such as in SEQ ID NO: 1) is preferably at least 1:1 (i.e., there is at least one hydrogen peroxide molecule per pair of Cys residues), optionally at least 2:1, optionally at least 3:1, and optionally at least 4:1. An exemplary molar ratio of hydrogen peroxide to pair of Cys residues (e.g., to peptide) is at about 5:1. Alternatively or additionally, hydrogen peroxide may optionally be added until no thiohydroxy groups remain (e.g., as determined by a suitable assay, such as an Ellman test).

In some of any of the respective embodiments described herein, the oxidizing is effected by contacting an aqueous solution comprising the peptide at a concentration of at least 5 mg/mL with hydrogen peroxide (e.g., according to any of the embodiments described herein relating to contact with hydrogen peroxide). In some such embodiments, a concentration of the peptide is in a range of from 5 to 20 mg/mL. In some embodiments, a concentration of the peptide is in a range of from 5 to 15 mg/mL. In some embodiments, a concentration of the peptide is in a range of from 5 to 10 mg/mL. An exemplary concentration of the peptide is about 10 mg/mL.

In some of any of the respective embodiments described herein, the oxidizing is effected by contacting an aqueous solution comprising the peptide at a concentration of at least 10 mg/mL with hydrogen peroxide (e.g., according to any of the embodiments described herein relating to contact with hydrogen peroxide). In some such embodiments, a concentration of the peptide is in a range of from 10 to 20 mg/mL. In some embodiments, a concentration of the peptide is in a range of from 10 to 15 mg/mL.

In some of any of the embodiments described herein relating to oxidation effected using an aqueous solution, the aqueous solution is mildly alkaline, for example, an aqueous solution of ammonium bicarbonate ($NH_4HCO_3$). An exemplary concentration of ammonium bicarbonate is about 0.1 M.

Peptide Isolation:

The process preferably further comprises isolating the peptide obtained according to any of the respective embodiments described herein (e.g., using a combination of any of the embodiments described herein relating to coupling, any of the embodiments describes herein relating to cleavage of the peptide from a resin, and any of the embodiments described herein relating to disulfide bond formation). Any suitable technique known in the art may optionally be used.

In some of any of the embodiments described herein, isolation of the peptide comprises chromatography, for example, at least one step (e.g., optionally one or two steps) of preparative high performance liquid chromatography (HPLC). In exemplary embodiments, a C18 column is used for effecting chromatography (e.g., HPLC).

In some of any of the embodiments described herein, isolation of the peptide comprises loading the peptide (e.g., in at least one step of HPLC described herein) on a reverse phase chromatography column (e.g., a C18 column) at a concentration of no more than 40 grams peptide per kg of the column (by weight of resin of the column).

In some of any of the embodiments described herein, isolation of the peptide comprises loading the peptide (e.g., in at least one step of HPLC described herein) on a reverse phase chromatography column (e.g., a C18 column) at a concentration of at least 4 grams peptide per kg of the column (by weight of resin of the column). In some such embodiments, the loading concentration is in a range of from 4 to 40 grams peptide per kg column resin. In some embodiments, the loading concentration is in a range of from 4 to 30 grams peptide per kg column resin. In some embodiments, the loading concentration is in a range of from 4 to 25 grams peptide per kg column resin.

In some of any of the embodiments described herein, isolation of the peptide comprises loading the peptide (e.g., in at least one step of HPLC described herein) on a reverse phase chromatography column (e.g., a C18 column) at a concentration of at least 10 grams peptide per kg of the column (by weight of resin of the column). In some such embodiments, the loading concentration is in a range of from 10 to 40 grams peptide per kg column resin. In some embodiments, the loading concentration is in a range of from 10 to 30 grams peptide per kg column resin. In some embodiments, the loading concentration is in a range of from 10 to 25 grams peptide per kg column resin.

In some of any of the embodiments described herein, isolation of the peptide comprises loading the peptide (e.g., in at least one step of HPLC described herein) on a reverse phase chromatography column (e.g., a C18 column) at a concentration of at least 20 grams peptide per kg of the column (by weight of resin of the column). In some such embodiments, the loading concentration is in a range of from 20 to 40 grams peptide per kg column resin. In some embodiments, the loading concentration is in a range of from 20 to 30 grams peptide per kg column resin. In some embodiments, the loading concentration is in a range of from 20 to 25 grams peptide per kg column resin.

The peptide loaded on a column (according to any of the respective embodiments described herein) is eluted, e.g., using a buffer solution (e.g., in combination with an acetonitrile gradient, according to any of the respective embodiments described herein). The pH of the buffer solution is optionally in a range of from 1.5 to 3, optionally from 2.0 to 2.5, and optionally about 2.25. In some embodiments, triethylammonium phosphate buffer is used to elute the peptide from the column, for example, at a concentration of at least about 0.01 M, or at least about 0.03 M, or at least about 0.1 M. In exemplary embodiments, the concentration of triethylammonium phosphate is about 0.1 M.

Elution from an HPLC column is optionally effected with an acetonitrile gradient. The gradient optionally comprises increasing a concentration of acetonitrile by a rate (which is optionally varied over time) in a range of from 0.1% acetonitrile per minute to 2% acetonitrile per minute, e.g., about 1% per 5-6 minutes and/or about 1% per minute. Alternatively or additionally, the gradient optionally comprises increasing a concentration of acetonitrile (e.g., from 0%) to a concentration in a range of from 10% to 40%, or from 20% to 30%, or to about 25%.

An exemplary gradient (e.g., using triethylammonium phosphate buffer according to any of the respective embodiments described herein) comprises 0% acetonitrile for about 8 minutes, from 0% to about 5% acetonitrile in about 5 minutes (e.g., a rate of about 1% per minute), and from about 5% to about 25% acetonitrile in about 120 minutes (e.g., a rate of about 0.17% per minute).

In some of any of the respective embodiments, eluted peptide is loaded on a column (according to any of the respective embodiments described herein) a second time and eluted, e.g., using a buffer solution (e.g., in combination with an acetonitrile gradient, according to any of the respective embodiments described herein). Acetic acid buffer (e.g., acetic acid/ammonium acetate) may optionally be used to elute the peptide from the column (e.g., in order to obtain the peptide as an acetate salt), for example, at a concentration of at least about 5 mM, or at least about 20 mM, or at least about 35 mM. In exemplary embodiments, the concentration of acetate is about 35 mM.

An exemplary gradient (e.g., using acetic acid buffer according to any of the respective embodiments described herein) for a second elution comprises 0% acetonitrile for 8 minutes, and from 0% to 22% acetonitrile in 110 minutes (a rate of 0.2% per minute).

The process optionally further comprises lyophilizing the peptide obtained by chromatography (e.g., according to any of the respective embodiments described herein).

Lyophilization within a large-scale process is optionally facilitated by the use of lyophilization trays (e.g., as exemplified herein) rather than flasks.

In some of any of the embodiments relating to lyophilization, the process further comprises grinding the peptide following lyophilization. Grinding may optionally be effected with the aid of beads (e.g., polypropylene beads), e.g., using a jar mill.

As exemplified herein, such grinding may advantageously enhance apparent density of the peptide (a.k.a. "densification") and/or ease of handling (e.g., during packaging), particularly when the lyophilized peptide prior to grinding has a "fluffy" consistency.

Additional Process Embodiments

According to some of any of the embodiments described herein, the process is characterized by at least one, or at least two, or at least three, or at least four, or at least five, or at least six of the following features (i)-(vii):

(i) coupling is effected using diisopropylcarbodiimide (DIC) in combination with ethyl cyanohydroxyiminoacetate and/or N-hydroxybenzotriazole (e.g., according to any of the respective embodiments described herein);

(ii) cleavage of the peptide from the resin is effected by contacting the linear peptide coupled to the resin with a solution comprising trifluoroacetic acid (TFA) and a scavenger which is dithiothreitol (DTT) and/or dithioerythritol (DTE) (e.g., according to any of the respective embodiments described herein);

(iii) the process further comprises precipitating the free linear peptide after cleaving without concentrating the free linear peptide by evaporation prior to precipitation of the peptide (e.g., according to any of the respective embodiments described herein);

(iv) oxidation comprises contacting an aqueous solution comprising the linear peptide at a concentration of at least 5 mg/mL with hydrogen peroxide (e.g., according to any of the respective embodiments described herein);

(v) isolating the peptide comprises loading the cyclic peptide on a reverse phase chromatography column at a concentration of no more than 40 grams cyclic peptide per kg of the column, and eluting the cyclic peptide from the column (e.g., according to any of the respective embodiments described herein);

(vi) isolating the cyclic peptide comprises lyophilization, and the process further comprises grinding the cyclic peptide following lyophilization (e.g., according to any of the respective embodiments described herein); and/or (vii) a degree of substitution of the resin used for peptide synthesis is at least 0.3 milliequivalents per gram and/or the resin is a Rink AMS resin (e.g., according to any of the respective embodiments described herein).

In some of any of the embodiments described herein, the process includes at least abovementioned features (i) and (ii) (optionally in combination with at least one of features (iii), (iv), (v), (vi) and/or (vii)), or at least abovementioned features (i) and (iii) (optionally in combination with at least one of features (iv), (v), (vi) and/or (vii)), or at least abovementioned features (i) and (iv) (optionally in combination with at least one of features (v), (vi) and/or (vii)), or at least abovementioned features (i) and (v) (optionally in combination with at least one of features (vi) and/or (vii)), or at least abovementioned features (i) and (vi) (optionally in combination with feature (vii)), or at least abovementioned features (i) and (vii).

In some of any of the embodiments described herein, the process includes at least abovementioned features (ii) and (iii) (optionally in combination with at least one of features (iv), (v), (vi) and/or (vii)), or at least abovementioned features (ii) and (iv) (optionally in combination with at least one of features (v), (vi) and/or (vii)), or at least abovementioned features (ii) and (v) (optionally in combination with at least one of features (vi) and/or (vii)), or at least abovementioned features (ii) and (vi) (optionally in combination with feature (vii)), or at least abovementioned features (ii) and (vii).

In some of any of the embodiments described herein, the process includes at least abovementioned features (iii) and (iv) (optionally in combination with at least one of features (v), (vi) and/or (vii)), or at least abovementioned features (ii) and (v) (optionally in combination with at least one of features (vi) and/or (vii)), or at least abovementioned features (iii) and (vi) (optionally in combination with feature (vii)), or at least abovementioned features (iii) and (vii).

In some of any of the embodiments described herein, the process includes at least abovementioned features (iv) and (v) (optionally in combination with at least one of features (vi) and/or (vii)), or at least abovementioned features (iv) and (vi) (optionally in combination with feature (vii)), or at least abovementioned features (iv) and (vii).

In some of any of the embodiments described herein, the process includes at least abovementioned features (v) and (vi) (optionally in combination with feature (vii)), or at least abovementioned features (iv) and (vii).

In some of any of the embodiments described herein, the process includes at least abovementioned features (vi) and (vii).

Formulation and Uses of Peptide:

The peptide prepared according to a process described herein (according to any of the respective embodiments) may optionally be for use in treatment of a condition treatable by the peptide.

According to an aspect of some embodiments of the invention, there is provided a use of a peptide prepared according to a process described herein (according to any of the respective embodiments) in the manufacture of a medicament for treating a condition treatable by the peptide.

According to an aspect of some embodiments of the invention, there is provided a method of treating a condition treatable by a peptide, the method comprising administering the peptide to subject in need thereof, wherein the peptide is prepared according to a process described herein (according to any of the respective embodiments).

In some of any of the embodiments described herein (according to any of the aspects described herein) the peptide is a peptide having SEQ ID NO: 1 (or an analog or derivative thereof), and the treatment comprises any treatment in which inhibiting CXCR4 is advantageous.

It is expected that during the life of a patent maturing from this application many relevant treatments will be developed and the scope of the terms "condition", "treatable by a peptide" and "treatment in which inhibiting CXCR4 is advantageous" is intended to include all such new technologies a priori.

In some of any of the embodiments described herein (according to any of the aspects described herein) the peptide is a peptide having SEQ ID NO: 1 (or an analog or derivative thereof), and the condition treatable by a peptide having SEQ ID NO: 1 (or an analog or derivative thereof) is a cancer or arthritis (e.g., chronic rheumatoid arthritis), e.g., as described in U.S. Pat. No. 7,423,007 (the contents of which are incorporated herein by reference, particularly contents regarding treatment of conditions by the aforementioned peptides)

Examples of conditions treatable (according to any of the aspects described herein) by a peptide having SEQ ID NO: 1 (or an analog or derivative thereof) include, without limitation, retinoblastoma and/or neuroectodermal derived tumors, e.g., as described in International Patent Application Publication WO 2012/095849 (the contents of which are incorporated herein by reference, particularly contents regarding treatment of conditions by the aforementioned peptides); large cell lung cancer, e.g., as described in WO 2013/160895 (the contents of which are incorporated herein by reference, particularly contents regarding treatment of conditions by the aforementioned peptides); multiple myeloma, microglioma and/or glioma, e.g., as described in International Patent Application Publication WO 2008/075370 (the contents of which are incorporated herein by reference, particularly contents regarding treatment of conditions by the aforementioned peptides); breast cancer and/or pancreatic cancer, e.g., as described in U.S. Pat. No. 7,423,007; thrombocytopenia, e.g., as described in International Patent Application Publication WO 2010/146578 (the contents of which are incorporated herein by reference, particularly contents regarding treatment of conditions by the aforementioned peptides); risk of bone marrow suppression, e.g., as described in International Patent Application Publication WO 2008/075369 (the contents of which are incorporated herein by reference, particularly contents regarding treatment of conditions by the aforementioned peptides); and HIV infection, e.g., as described in U.S. Pat. No. 8,435,939 (the contents of which are incorporated herein by reference, particularly contents regarding treatment of conditions by the aforementioned peptides).

Suitable analogs and derivatives of the peptide having SEQ ID NO: 1 are described in U.S. Pat. Nos. 7,423,007 and 8,435,939 and International Patent Application Publications WO 2008/075369, WO 2008/075370, WO 2010/146578, WO 2012/095849 and WO 2013/160895 (the contents of each of which are incorporated herein by reference, particularly contents regarding analogs and derivatives of SEQ ID NO: 1).

The peptide of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the peptide accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of peptide effective to prevent, alleviate or ameliorate symptoms of a disorder (e.g., a cancer or arthritis, as discussed herein) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide levels of the active ingredient sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Additional Definitions:

As used herein the term "about" refers to ±20%. In some of any of the respective embodiments described herein, the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Reference Example 1

Solid Phase Synthesis of BL-8040 According to U.S. Pat. No. 7,423,007

The following procedure, as described in U.S. Pat. No. 7,423,007 was used to prepare 551 mg of the cyclic peptide BL-8040 (SEQ ID NO: 1).

The cyclic peptide BL-8040 was prepared by solid phase synthesis, wherein solid phase synthesis reaction steps were repeated 14 times for the construction of the entire peptide, beginning with the C-terminal amino acid and ending with the N-terminal amino acid. Each amino acid addition was performed in two steps: the first step includes the removal of the Fmoc protective group from the N-terminus of the last amino acid added to the peptide sequence (or from the resin, when adding the first amino acid), followed by attachment of the sequential amino acid to the elongating of the peptide on the resin. The last residue to be added to the peptide on the resin was the 4-fluorobenzoyl group, which does not contain an Fmoc group.

Resin:
The resin was 2.94 grams Fmoc-Rink amide resin with 0.34 mmol/gram substitution, i.e., 1 mmol.

Removal of Fmoc Protective Group:
The Fmoc protective group was removed from the N-terminus (of the last amino acid added to the peptide sequence) or resin using a solution of 20% piperidine in dimethylformamide (DMF).

Attachment of Amino Acid:
The amino acids were coupled in the form of appropriate amino acid derivatives, using diisopropylcarbodiimide (DIC) in combination with HOBt (N-hydroxybenzotriazole) in DMF. Cys, Arg, Tyr and Lys (D-Lys or L-Lys) were protected as Cys(Trt), Arg(Pbf), Tyr(t-Bu) and Lys(Boc) (D- or L-), respectively. In the final step, 4-fluorobenzoic acid was coupled instead of an amino acid. Amounts of amino acid (or 4-fluorobenzoic acid) used were 2.5 equivalents.

In-process monitoring of the condensation reaction was performed using the ninhydrin test of Kaiser et al. [*Anal Biochem* 1970, 34:595-598].

Cleavage and Deprotection:
Cleavage of the peptide (1 mmol) from the resin and removal of protection groups was performed by treatment with 270 mL of 1 M TMSBr-thioanisole/trifluoroacetic acid (TFA) mixture in the presence of m-cresol (100 equivalents) and ethanedithiol (300 equivalents) at 25° C. for 3 hours.

The resin was separated by filtration and washed twice with TFA (5 mL).

The mixture of filtrate and wash solution was subjected to concentration by vacuum.

The peptide was then combined with 300 mL water-cooled dry ether, and the resulting sediment was separated by centrifugal sedimentation and decantation.

The crude product was washed with cold ether, dissolved in 500 mL of 1 N acetic acid, and diluted to 2.5 L by distilled water.

Oxidative Cyclization:
Dilute water solution of the crude linear peptide was adjusted to pH 7.5 by concentrated ammonia water, and oxidation was effected by ventilated air oxidation.

Preparative HPLC:
The solution obtained upon completion of the cyclization step was purified by separation on a preparative HPLC C18 column (Cosmosil™ 5C18-AR-II) with acetonitrile and water, and by gel filtration chromatography (Sephadex™ G-15) with 0.1 N acetic acid eluate.

A polypeptide of a single peak was obtained and freeze-dried.

Purity was confirmed by HPLC.
Yield was 551.5 mg (19.4%).

Example 1

Large Scale Phase Synthesis of BL-8040

The cyclic peptide BL-8040 was prepared by large scale (825 mmol) solid phase synthesis, wherein solid phase synthesis reaction steps were repeated 14 times for the construction of the entire peptide, beginning with the C-terminal amino acid and ending with the N-terminal amino acid. Each amino acid addition was performed in two steps: the first step includes the removal of the Fmoc protective group from the N-terminus of the last amino acid added to the peptide sequence (or from the resin, when adding the first amino acid), followed by attachment of the sequential amino acid to the elongating of the peptide on the resin. The last residue to be added to the peptide on the resin was the 4-fluorobenzoyl group, which does not contain an Fmoc group.

The final yield was 468 grams (25%)
Resin:
The resin was Fmoc-Rink AMS resin with substitution in a range of 0.3 to 0.6 milliequivalents/gram.

Removal of Fmoc Protective Group:
The Fmoc protective group was removed from the N-terminus (of the last amino acid added to the peptide sequence)

or resin using a solution of 20% piperidine in dimethylformamide (DMF) (10 ml per gram of initial resin). Washing with DMF removed the piperidine solution prior to the next amino acid reaction, confirmed by testing pH of the wash.

Attachment of Amino Acid:

The amino acids were coupled in the form of an appropriate amino acid derivative, using diisopropylcarbodiimide (DIC) in combination with HOBt (N-hydroxybenzotriazole) as the activating agent. Cys, Arg, Tyr and Lys (D-Lys or L-Lys) were protected as Cys(Trt), Arg(Pbf), Tyr(t-Bu) and Lys(Boc) (D- or L-), respectively. In the final step, 4-fluorobenzoic acid was coupled instead of an amino acid. Calculations of amino acid (or 4-fluorobenzoic acid), DIC and HOBt quantities were based on a two-fold excess of the substitution and batch size.

In-process monitoring, using the ninhydrin and chloranil tests was performed at the end of each cycle for evaluation of the coupling step. A negative test result indicates the absence of free amino groups (complete coupling). If the test is positive, indicating unreacted amino groups (incomplete coupling), the coupling reaction may be prolonged, or re-coupling of the protected amino acid derivative may be performed.

After the synthetic cycles were complete, the resin-peptide was washed with a solution of DMF/isopropanol (1:1) and dried with nitrogen.

Cleavage and Deprotection:

Cleavage was performed to detach the peptide molecule from its supportive resin and to remove the protective group. An acidolysis reaction was performed with 95% trifluoroacetic acid (TFA) with 5% water and 50 mg/mL dithioerythritol (DTE) as scavenger (10 mL TFA-based cleavage solution per gram of resin), e.g., for 3.25-3.5 hours at ambient temperature.

The resin was then filtered and rinsed twice with TFA in order to complete the extraction of the peptide.

The peptide solution volume was reduced under vacuum in a rotary evaporator (at about 35° C.) to a volume of about 30-35% of the original volume.

The peptide was then precipitated with a chilled mixture (−10±5° C.) of tert-butyl methyl ether (MTBE)/hexane (60:40 v/v) at a volume of 32 mL per gram resin.

The crude product was isolated by filtration, washed with MTBE and dried on the filter under a nitrogen stream to remove most of the solvent.

The obtained crude (linear) peptide was then solubilized in 90% acetic acid, the obtained solution was distributed in lyophilization flasks, shell frozen and lyophilized to dryness on a manifold lyophilizer, The peptide was analyzed by RP-HPLC for purity and by mass spectral analysis for confirmation of identity.

Oxidative Cyclization:

The crude linear peptide was cyclized by oxidation with hydrogen peroxide in a 0.1 M ammonium bicarbonate ($NH_4HCO_3$) solution, as follows:

The crude linear peptide was dissolved in 0.1 M $NH_4HCO_3$ at a concentration of 10 mg/mL, and an equal volume of 0.1 M $NH_4HCO_3$ was added to dilute the peptide to concentration of 5 mg/mL.

A solution of 1.5% hydrogen peroxide in water (5-fold excess) was then added dropwise to the peptide solution over a period of 25-30 minutes. The reaction was monitored using an Ellman test to confirm the absence of free sulfhydryl groups.

After completion of the reaction, the reaction mixture was acidified to pH 2-3 by addition of neat TFA and the resulting solution was used "as is" in the TEAP (triethylammonium phosphate) purification step.

First Preparative HPLC Columns (TEAP Purification):

The solution obtained upon completion of the cyclization step was purified by separation on a preparative RP-HPLC C18 column, 10 μm, 120 Å Daisogel™, loading about 2.4 L solution, containing about 11.7 grams crude peptide per kg resin.

The peptide was eluted with 0.1 M triethylammonium phosphate (TEAP) buffer (pH 2.25) and an acetonitrile (ACN) gradient. The gradient was as follows: 0% acetonitrile for 8 minutes, from 0% to 5% acetonitrile in 5 minutes (a rate of 1% per minute), and from 5% to 25% acetonitrile in 120 minutes (a rate of 0.17% per minute).

Elution fractions were collected, sampled and tested by HPLC to determine which fractions were pure enough (>95%) to be pooled for the second chromatography purification step. Hydrophilic and hydrophobic fractions of the first RP-HPLC purification that do not meet the purity acceptance criterion are retained and may be re-processed to maximize overall yield.

Second Preparative HPLC Columns (Acetic Acid Purification):

Purified fractions obtained from TEAP injections were pooled, diluted 1:1 with water, and the peptide was separated on a 10 μm, 120 Å Daisogel™ C18 column, loaded at a volume of about 2.7 L per kg resin and eluted with a 35 mM acetic acid based buffer and acetonitrile gradient. The gradient was as follows: 0% acetonitrile for 8 minutes, and from 0% to 22% acetonitrile in 110 minutes (a rate of 0.2% per minute). The column was washed with four column volumes of 0.1 M ammonium acetate after loading of the peptide and prior to the start of the elution gradient to obtain the peptide as an acetate salt.

Fraction collections were monitored by UV absorption at 230 nm. Elution fractions were collected, sampled and tested by HPLC to determine which fractions were pure enough to be pooled. Only fractions that met in-process control criteria (>98% purity by HPLC, and no unknown impurity ≥0.14%) were pooled. Pooled fractions of each chromatography cycle were lyophilized as sub-lots. Hydrophilic and hydrophobic fractions of the second RP-HPLC purification that do not meet the purity acceptance criterion are retained and may be re-processed to maximize overall yield.

Wet Pooling and Lyophilization:

All sub-lots that met the in-process control criteria of purified material were reconstituted in purified water at a concentration of approximately 50 g/L. The resulting solution was filtered on 0.2 μm PVDF filters prior to lyophilization.

Lyophilization was effected in 1200 mL lyophilization flasks, which were filled with an approximately equal volume of 100 mL per flask to obtain 5 grams of purified peptide per flask, and then shell-frozen in a dry ice/IPA bath with a condenser temperature of <−60° C. and a vacuum of <500 millitorrs. Lyophilization was performed for 65 to 85 hours.

After lyophilization, a sample was taken for measurement of acetate content. If not within the specified 11-15%, the bulk drug substance may be re-suspended in water and lyophilization repeated.

Densification:

The lyophilized material was placed in a polyethylene bottle with polypropylene "grinding" beads and the bottle placed on a jar mill for 20±5 minutes. This operation eliminates the "fluffiness" by increasing the apparent density and facilitates ease of handling of the bulk drug substance during packaging.

Packaging and Storage:

The final bulk drug substance was packaged in Type III depyrogenated amber glass bottles fitted with Teflon-lines polypropylene caps. Packaging was performed under a controlled humidity environment (15-30% relative humidity) to mitigate the uptake of water. Bottles were placed in aluminum laminated bags with a desiccant between two packing materials as a secondary container. The BL-8040 drug substance was then stored at −20±5° C.

Example 2

Modified Large Scale Solid Phase Synthesis of BL-8040

The cyclic peptide BL-8040 is prepared by large scale solid phase synthesis (e.g., at least about 500 grams of product), wherein solid phase synthesis reaction steps are repeated 14 times for the construction of the entire peptide, beginning with the C-terminal amino acid and ending with the N-terminal amino acid. Each amino acid addition is performed in two steps: the first step includes the removal of the Fmoc protective group from the N-terminus of the last amino acid added to the peptide sequence (or from the resin, when adding the first amino acid), followed by attachment of the sequential amino acid to the elongating of the peptide on the resin. The last residue to be added to the peptide on the resin is the 4-fluorobenzoyl group, which does not contain an Fmoc group. Steps of solid phase synthesis according to some embodiments are depicted in FIG. 1.

Resin:

The resin is Fmoc-Rink AMS resin with substitution in a range of from 0.6 to 0.9 milliequivalents/gram (as opposed to 0.6 milliequivalents/gram or less as described hereinabove).

Removal of Fmoc Protective Group:

The Fmoc protective group is removed from the N-terminus (of the last amino acid added to the peptide sequence) or resin using a solution of 20% piperidine in dimethylformamide (DMF) (about 8 ml per gram of initial resin). Washing with DMF removes the piperidine solution prior to the next amino acid reaction, confirmed by testing pH of the wash.

Attachment of Amino Acid:

The amino acids are coupled in the form of an appropriate amino acid derivative, using diisopropylcarbodiimide (DIC) in combination with ethyl cyanohydroxyiminoacetate (in contrast to HOBt as described hereinabove) as the activating agent. Cys, Arg, Tyr and Lys (D-Lys or L-Lys) are protected as Cys(Trt), Arg(Pbf), Tyr(t-Bu) and Lys(Boc) (D- or L-), respectively. In the final step, 4-fluorobenzoic acid is coupled instead of an amino acid. Calculations of amino acid (or 4-fluorobenzoic acid), DIC and ethyl cyanohydroxyiminoacetate quantities are based on a two-fold excess of the substitution and batch size.

In-process monitoring, using the ninhydrin and chloranil tests is performed at the end of each cycle for evaluation of the coupling step. A negative test result indicates the absence of free amino groups (complete coupling). If the test is positive, indicating unreacted amino groups (incomplete coupling), the coupling reaction may be prolonged, re-coupling of the protected amino acid derivative may be performed, or acetylation (capping) may be performed, e.g., using acetic anhydride in the presence of diisopropylethylamine (DIEA).

After the synthetic cycles are complete, the resin-peptide is washed with a solution of DMF/isopropanol (1:1) and dried with nitrogen.

Cleavage and Deprotection:

Cleavage is performed to detach the peptide molecule from its supportive resin and to remove the protective group. The acidolysis reaction is performed with 95% trifluoroacetic acid (TFA) with 5% water and 50 mg/mL scavenger (10 mL TFA-based cleavage solution per gram of resin), e.g., for 3.25-3.5 hours at ambient temperature. The scavenger is dithiothreitol (DTT), as opposed to dithioerythritol as described in Example 1 or ethanedithiol as described in Comparative Example 1.

The resin is then filtered and rinsed twice with TFA in order to complete the extraction of the peptide.

(In contrast to Example 1, no reduction of peptide solution volume is performed at this stage.)

The peptide is then precipitated with a chilled mixture (−10±5° C.) of tert-butyl methyl ether (MTBE)/hexane (60:49 v/v) at a volume of 45 mL per gram resin (rather than 32 mL per gram as described in Example 1).

The crude product is isolated by filtration, washed with MTBE and dried on the filter under a nitrogen stream to remove most of the solvent.

The obtained crude (linear) peptide is then dried under vacuum or solubilized with acetic acid and lyophilized (e.g., as described in Example 1).

The peptide is optionally analyzed by RP-HPLC for purity and/or by mass spectral analysis for confirmation of identity.

Oxidative Cyclization:

The crude linear peptide is cyclized by oxidation with 1.5% hydrogen peroxide in a 0.1 M ammonium bicarbonate ($NH_4HCO_3$) solution, at a peptide concentration of 10 mg/mL. In contrast to Example 1, the peptide was not further diluted to 5 mg/mL over a period of 25-30 minutes. The reaction is monitored using an Ellman test to confirm the absence of free sulfhydryl groups.

After completion of the reaction, the reaction mixture is acidified to pH 2-3 by addition of neat TFA and the resulting solution is used "as is" in the TEAP (triethylammonium phosphate) purification step.

First Preparative HPLC Columns (TEAP Purification):

The solution obtained upon completion of the cyclization step is purified by separation on a preparative RP-HPLC C18 column, 10 μm, 120 Å Daisogel™, loading about 2.4 L solution, containing about 20 to about 25 grams crude peptide per kg resin (as opposed to about 11.7 grams/kg, as described in Example 1).

The peptide is eluted with 0.1 M triethylammonium phosphate (TEAP) buffer (pH 2.25) and an acetonitrile (ACN) gradient.

Elution fractions are collected, sampled and tested by HPLC to determine which fractions are pure enough (≥95%) to be pooled for the second chromatography purification step. Hydrophilic and hydrophobic fractions of the first RP-HPLC purification that do not meet the purity acceptance criterion are retained and may be re-processed to maximize overall yield.

Second Preparative HPLC Columns (Acetic Acid Purification):

Purified fractions obtained from TEAP injections are pooled, diluted 1:1 with water, and the peptide is separated on a 10 μm, 120 Å Daisogel™ C18 column and eluted with a 35 mM acetic acid based buffer and acetonitrile gradient. The column is washed with four column volumes of 0.1 M ammonium acetate after loading of the peptide and prior to the start of the elution gradient to obtain the peptide as an acetate salt.

Fraction collections are monitored by UV absorption at 230 nm. Elution fractions are collected, sampled and tested by HPLC to determine which fractions are pure enough to be pooled. Only fractions that meet in-process control criteria (≥98% purity by HPLC, and no unknown impurity ≥0.14%) are pooled. Pooled fractions of each chromatography cycle are lyophilized as sub-lots. Hydrophilic and hydrophobic fractions of the second RP-HPLC purification that do not meet the purity acceptance criterion are retained and may be re-processed to maximize overall yield.

Wet Pooling and Lyophilization:

All sub-lots that meet the in-process control criteria of purified material are reconstituted in purified water at a concentration of approximately 50 g/L. The resulting solution is filtered on 0.2 μm PVDF filters prior to lyophilization.

Lyophilization is effected in lyophilization trays (e.g., of about 1.0 to about 1.2 liters per tray) in a vacuum of ≤150 millitorrs (e.g., for about 89 hours), rather than flasks as described in Example 1. The use of trays may enhance control of the process, facilitate higher scales and/or reduce in-process controls.

After lyophilization, a sample is taken for measurement of acetate content. If not within the specified 11-15%, the bulk drug substance is optionally re-suspended in water and lyophilization repeated.

Densification:

The lyophilized material is optionally subjected to densification according to procedures described in Example 1.

Packaging and Storage:

The final bulk drug substance is optionally packaged and/or stored according to procedures described in Example 1.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A large-scale process of preparing a cyclic peptide having SEQ ID NO: 1, or a pharmaceutically acceptable salt thereof, the process comprising:
  (a) sequentially coupling amino acids and 4-fluorobenzoic acid to a resin by solid phase peptide synthesis, thereby obtaining a linear peptide coupled to said resin;
  (b) cleaving said linear peptide from said resin, thereby obtaining a free linear peptide;
  (c) oxidizing cysteine residues of said linear peptide to form an intramolecular disulfide bond, thereby obtaining the cyclic peptide having SEQ ID NO: 1 in solution; and
  (d) isolating the cyclic peptide having SEQ ID NO: 1, or a pharmaceutically acceptable salt thereof,
  wherein:
  (i) said coupling is effected using diisopropylcarbodiimide (DIC) in combination with ethyl cyanohydroxyiminoacetate and/or N-hydroxybenzotriazole;
  (ii) said cleaving is effected by contacting said linear peptide coupled to said resin with a solution comprising trifluoroacetic acid (TFA) and a scavenger selected from the group consisting of dithioerythritol (DTE) and dithiothreitol (DTT);
  (iii) the process further comprises precipitating said free linear peptide after said cleaving without concentrating said free linear peptide by evaporation prior to said precipitating;
  (iv) said oxidizing is effected by contacting an aqueous solution comprising said linear peptide at a concentration of at least 5 mg/mL with hydrogen peroxide;
  (v) said isolating comprises loading said cyclic peptide on a reverse phase chromatography column at a concentration of no more than 40 grams cyclic peptide per kg of said column, and eluting said cyclic peptide from said column;
  (vi) said isolating the cyclic peptide having SEQ ID NO: 1 comprises lyophilization, and the process further comprises grinding said cyclic peptide following said lyophilization; and/or
  (vii) a degree of substitution of said resin is at least 0.3 milliequivalents per gram and/or said resin is a Rink aminomethylstyrene resin.

2. The process of claim 1, wherein said coupling is effected using diisopropylcarbodiimide (DIC) in combination with ethyl cyanohydroxyiminoacetate and/or N-hydroxybenzotriazole.

3. The process of claim 1, wherein said DIC and said ethyl cyanohydroxyiminoacetate and/or N-hydroxybenzotriazole are used in a molar excess of about two-fold.

4. The process of claim 1, wherein a concentration of said scavenger in said solution comprising said scavenger is in a range of from 10 mg/mL to 500 mg/mL.

5. The process of claim 1, wherein said cleaving is effected by contacting said linear peptide coupled to said resin with a solution comprising trifluoroacetic acid (TFA) and a scavenger selected from the group consisting of dithioerythritol (DTE) and dithiothreitol (DTT).

6. The process of claim 5, wherein a concentration of dithiothreitol in said solution is about 50 mg/mL.

7. The process of claim 1, further comprising precipitating said free linear peptide after said cleaving without concentrating said free linear peptide by evaporation prior to said precipitating.

8. The process of claim 1, wherein said precipitating is effected by addition of a mixture of tert-butyl methyl ether (MTBE) and hexane at a volume of about 45 mL of said mixture per gram of said resin.

9. The process of claim 1, wherein said oxidizing is effected by contacting said linear peptide with hydrogen peroxide.

10. The process of claim 9, wherein said contacting is effected by contacting an aqueous solution comprising said linear peptide at a concentration of at least 5 mg/mL with hydrogen peroxide.

11. The process of claim 1, wherein said isolating comprises loading said cyclic peptide on a reverse phase chromatography column at a concentration of no more than 40 grams cyclic peptide per kg of said column, and eluting said cyclic peptide from said column.

12. The process of claim 1, wherein said column is a C18 column.

13. The process of claim 1, wherein said eluting is effected with triethylammonium phosphate solution.

14. The process of claim 1, wherein said isolating the cyclic peptide having SEQ ID NO: 1 comprises lyophilization, and the process further comprises grinding said cyclic peptide following said lyophilization.

15. The process of claim 1, wherein a degree of substitution of said resin is at least 0.3 milliequivalents per gram and/or said resin is a Rink aminomethylstyrene resin.

* * * * *